United States Patent [19]

Peterson et al.

[11] Patent Number: 5,484,706
[45] Date of Patent: Jan. 16, 1996

[54] IMMUNOASSAY FOR ANALYTES IN SAMPLES USING ALKYLATING AGENTS

[75] Inventors: Jon E. Peterson, Minnetonka; Jeffrey W. Steaffens, Chanhassen, both of Minn.

[73] Assignee: Pasteur Sanofi Diagnostics, Marnes-la-Coquette, France

[21] Appl. No.: 65,019

[22] Filed: May 19, 1993

[51] Int. Cl.$^6$ .................... G01N 33/571; G01N 33/569
[52] U.S. Cl. .................... 435/7.36; 435/7.35; 435/7.37; 435/962; 436/825
[58] Field of Search .................... 436/825; 435/962, 435/7.35, 7.36, 7.37

[56] References Cited

U.S. PATENT DOCUMENTS

| | | | |
|---|---|---|---|
| 4,427,782 | 1/1984 | Caldwell et al. | 436/542 |
| 4,497,899 | 2/1985 | Armstrong et al. | 436/510 |
| 4,617,264 | 10/1986 | Whiteley et al. | 436/534 |
| 4,652,518 | 3/1987 | Makela et al. | 436/519 |
| 4,663,291 | 5/1987 | Rose | 436/510 |
| 4,703,001 | 10/1987 | Vodian et al. | 435/810 |
| 4,766,065 | 8/1988 | Mosier et al. | 435/34 |
| 4,830,960 | 5/1989 | Appleton | 435/21 |
| 4,916,057 | 4/1990 | Thompson et al. | 436/825 |
| 4,978,632 | 12/1990 | Mach et al. | 436/825 |
| 5,075,221 | 12/1991 | Mauck et al. | 435/7.36 |
| 5,187,066 | 2/1993 | Becker et al. | 435/7.36 |
| 5,187,107 | 2/1993 | Watkins et al. | 436/505 |
| 5,219,890 | 6/1993 | Boucher | 514/705 |

FOREIGN PATENT DOCUMENTS

| | | |
|---|---|---|
| 0174106 | 3/1986 | European Pat. Off. . |
| 2047889 | 12/1980 | United Kingdom . |

OTHER PUBLICATIONS

M. Walder et al., Acta path. microbiol. immunolog. scand. Sect. B, vol. 90, pp. 423–433 (1982).

R. W. Peeling, et al, "Neutralization of Chlamydia trachomatis: Kinetics and Stoichiometry", *Infection and Immunity*, vol. 59, No. 8, (Aug. 1991), pp. 2624–2630.

P. Nishanian, et al, "A Simple Method for Improved Assay Demonstrates That HIV p24 Antigen is Present as Immune Complexes in Most Sera from HIV–Infected Individuals", *The Journal of Infectious Diseases*, (1990), 162:21–28.

T. Mathiesen, et al, "Acid hydrolysis of serum samples to increase detection of HIV antigen", *Journal of Virological Methods*, 22 (1988), pp. 143–148.

H. Caldwell, et al, "Monoclonal Antibody Against a Genus–Specific Antigen of Chlamydia Species: Location of the Epitope on Chlamydial Lipopolysaccharide", *Infection and Immunity*, (May 1984), pp. 306–314.

Primary Examiner—Mary E. Ceperley
Attorney, Agent, or Firm—Fredrikson & Byron

[57] ABSTRACT

An improved immunoassay method and kit have been developed that include a sample pretreatment method and kit employing an alkylating agent that modifies antibodies in the sample to render the antibodies incapable of interfering with analyte detection. Prior to performing the immunoassay, the alkylating agent is inactivated so that it does not modify antibody reagents used in the immunoassay.

14 Claims, 3 Drawing Sheets

IMMUNOASSAY FOR ANALYTES IN SAMPLES USING ALKYLATING AGENTS

FIELD OF INVENTION

This invention relates to an improved immunoassay for detecting the presence or amount of an analyte in a patient sample. More particularly, the invention relates to the use of alkylating agents at a neutral or alkaline pH in an improved immunoassay method for detecting analytes in a sample containing endogenous antibodies.

BACKGROUND OF THE INVENTION

Over the past two decades, immunoassay or immunocytochemical assay methods have been developed which are useful in determining whether a particular analyte is present in a patient sample. In a typical immunoassay, an assay reagent is labeled with a compound that is capable of producing a detectable signal and that reagent is combined with a patient sample suspected of containing a particular analyte. The labeled assay reagent will bind to the analyte in an amount related to the amount of analyte in the sample.

Endogenous anti-analyte antibodies and immune complexes of antibodies and analyte circulating in serum samples have been found to interfere with analyte detection immunoassays. U.S. Pat. No. 4,703,001, describes a pretreatment method for disassociating immune complexes and denaturing anti-analyte antibodies for immunoassays for acid stable analytes in a serum sample comprising contacting the serum sample a pH dependent chaotrope at an acid pH. Similarly, P. Nishanian, et al. in J. Infect. Dis. 162:21–28 (1990), describe an acid hydrolysis serum sample pretreatment method that was used to disassociate analyte-anti-HIV antibodies immune complexes and denature anti-HIV antibodies. In order to obtain complete denaturation of the anti-HIV antibodies, however, the test serum was treated at 37° C. for 60 minutes with a 0.5N HCl solution.

While acid hydrolysis, as performed for protein or peptide antigens, as described above, may provide accurate results, it is always desirable to achieve those results faster and with increased sensitivity. Moreover, such rigorous acid hydrolysis would not be permissible with some analytes. For example, the 2-keto-3-deoxyoctulosonic acid (KDO) sugars of lipopolysaccharide (LPS) antigens from certain microorganisms would be hydrolyzed by such treatment, thus destroying their antigenic activity. It would, therefore, be desirable to have an immunoassay method in which endogenous antibodies present in a patient sample can be irreversibly denatured at a pH greater than 7.0 and desirably at an alkaline pH without effecting the antigenicity of the analyte.

SUMMARY OF THE INVENTION

The performance of immunoassays for the analysis of analytes in a patient sample can be significantly improved by the pretreatment of the sample to modify endogenous antibodies to reduce or prevent interference of analyte detection by the antibodies. As mentioned above, such antibodies and immune complexes can interfere with analyte specific binding steps of many immunoassays. The sample pretreatment step of the invention employs alkylating agents which are active at a pH greater than 7.0, and preferably at an alkaline pH greater than 8.0. Alkylating agents of this invention are active at a neutral or alkaline pH and do not effect the antigenicity of the analyte. Desirably, the alkylating agent acts on lysine, arginine or primary amine groups of the antibodies to modify groups on the antibodies to prevent them from interfering with analyte detection and include without limitation gluteraldehyde, O-methylisourea, formaldehyde, butanedione, cyclohexanedione and S-acetyl thioglycolic acid N-hydroxy succinimide.

Prior to performing the immunoassay, said alkylating agent is inactivated so that it does not effect the reagents of the immunoassay. The means for inactivating the alkylating agent will vary based upon the alkylating agent used. One type of alkylating agent useful with this invention is active at an alkaline pH and inactive at a neutral pH. This type of alkylating agent is particularly useful in detecting analytes that are present in sample in a form that requires the sample to be pretreated with an alkaline detergent solution to extract the analyte.

In one embodiment, sample is pretreated with the alkylating agent following an alkaline detergent extraction conducted prior to an immunoassay for chlamydial LPS, or similar antigens. The alkylating agent should be added prior to neutralization of the sample solution. In a preferred embodiment, an alkylating agent active only at an alkaline pH is added after the alkaline extraction and incubated with the sample solution for a sufficient time to allow endogenous antibodies to be modified so that the antibodies will be unable to interfere with analyte detection during the immunoassay. The alkylating agent must be chosen so that it will be compatible with the other reagents used to extract the analyte. Following the incubation, the alkylating agent is inactivated by neutralization of the sample solution and the immunoassay performed.

In one embodiment, the analyte to be determined is acid sensitive. For purposes of this invention, "acid sensitive" means an analyte that loses its antigen activity when incubated in a solution having a pH less than 3.0. For purposes of this application, acid sensitive analytes include without limitation LPS antigens having a KDO moiety, from *Chlamydia trachomatis*, *Chlamydia psittaci*, *Salmonella typhimurium*, *Neisseria gonorrhoeae* and *Escherichia coli*.

In a particularly preferred embodiment, an immunoassay for LPS antigen is performed and after the antigen extraction step, the alkylating agent combined with dithiothreitol (DTT) is added. DTT is a mucolytic agent as well as a chemical modifier that binds to cysteine. The use of DTT in combination with an alkylating agent enhances the stability of signal over time and increases the sensitivity of the assay.

Another embodiment of the invention includes a immunoassay kit for use in assaying an analyte in a patient sample containing endogenous antibodies that interfere with analyte detection, the kit comprising immunoassay reagents for performing an immunoassay on the sample to assay the analyte, an alkylating agent capable of alkylating groups on the antibodies at a pH not less than 7.0 to prevent the endogenous antibodies from interfering with analyte detection. The kit further comprises an inactivating agent that is capable of inactivating the alkylating agent so that it no longer modifies antibodies. In one embodiment, wherein the alkylating agent is active only at an alkaline pH, the inactivating agent is a neutralizing agent.

DETAILED DESCRIPTION OF THE INVENTION

Figure 1:
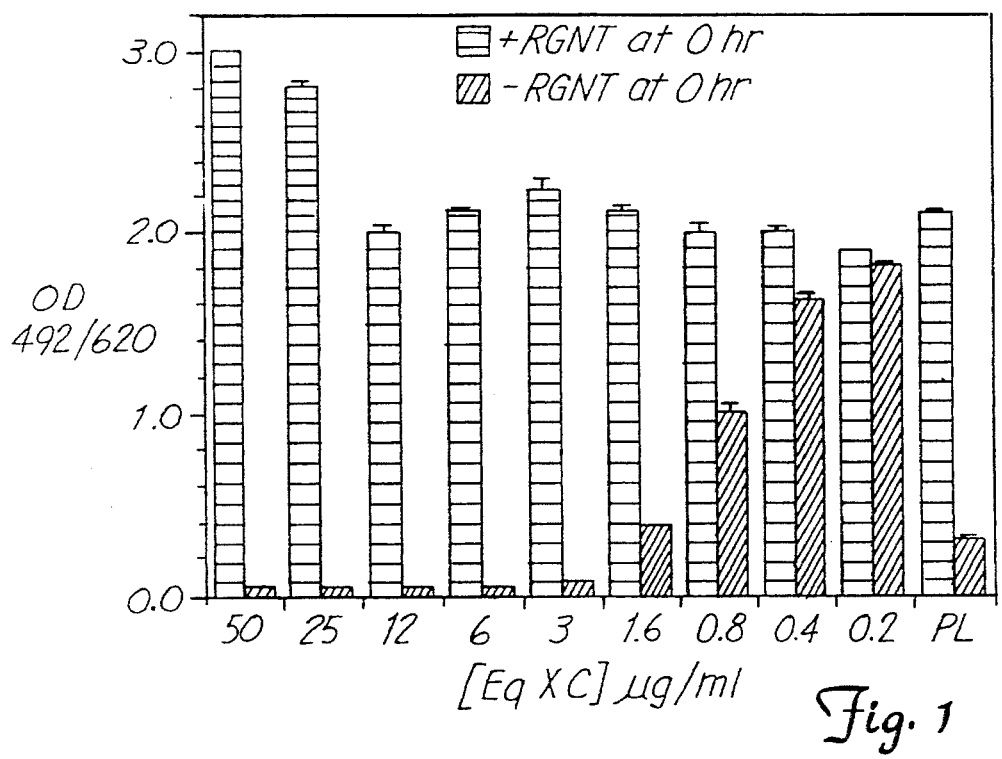
FIG. 1 is a graph showing the effect of the pretreatment method of the invention on analyte detection immediately after extraction.
Figure 2:
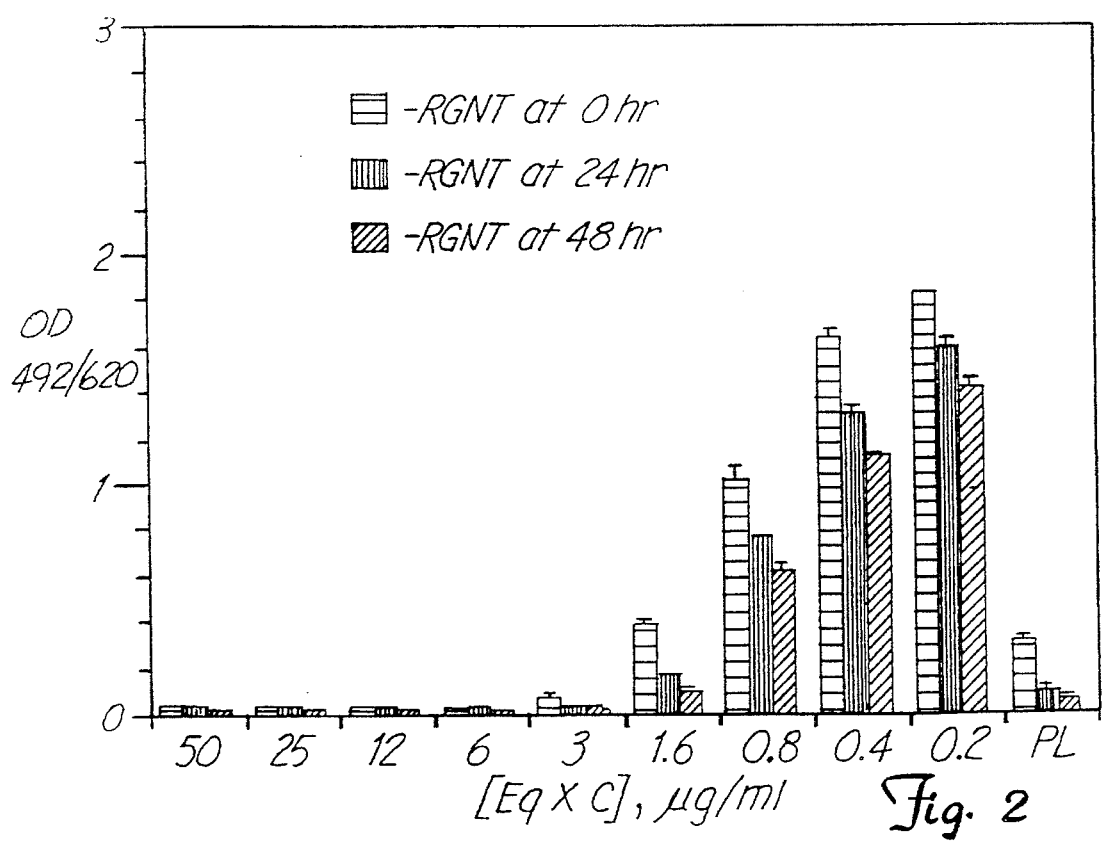
FIG. 2 is a graph showing the interference with analyte detection at various times after extraction without use of the pretreatment method of the invention.
Figure 3:
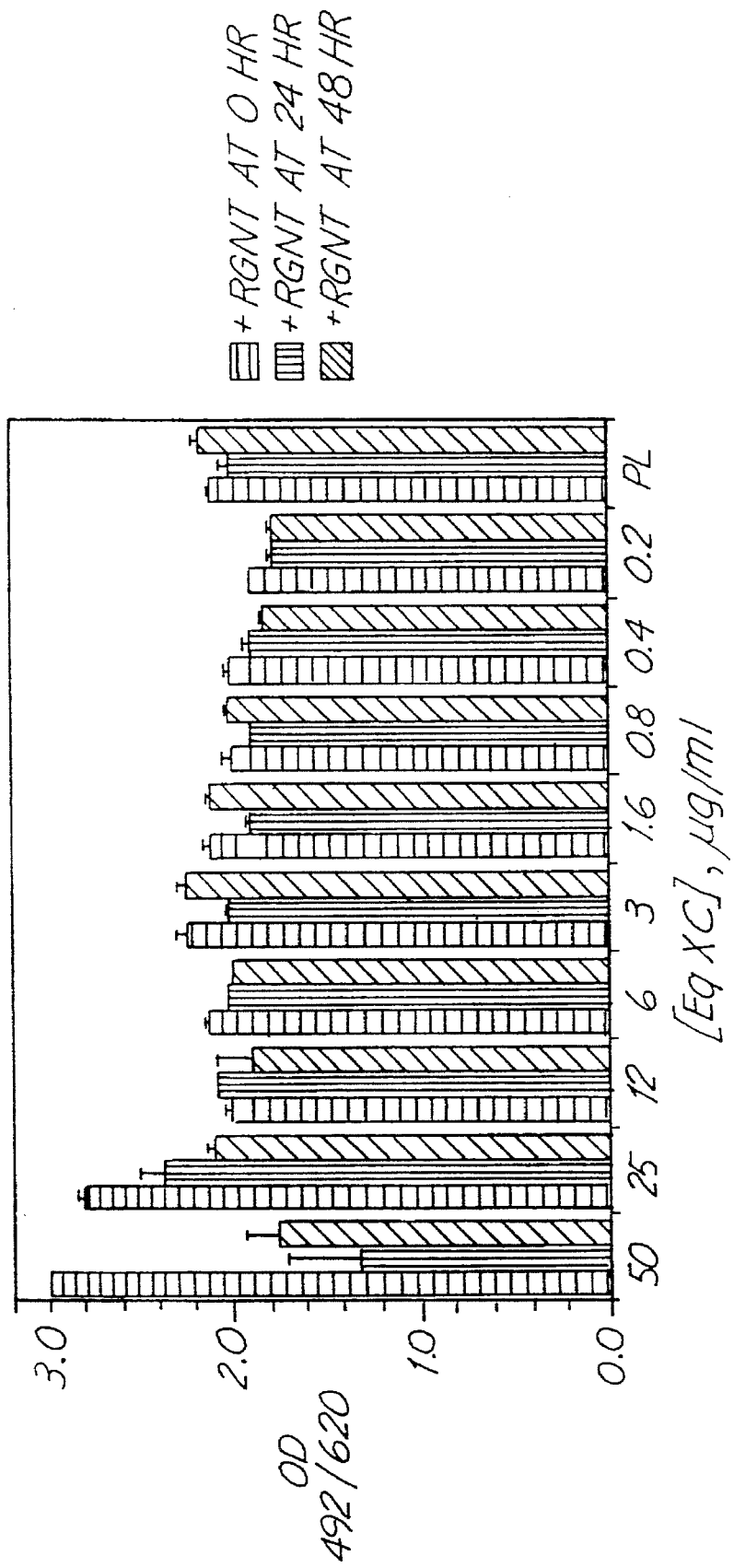
FIG. 3 is a graph showing the effects of the pretreatment method of the invention on analyte detection at various times after extraction.
Figure 4:
FIG. 4 shows Western Blot strips demonstrating effect of the alkylating agents of the invention on the ability of anti-chlamydia antibodies in patient samples to bind to analyte.

The reagents and methods of this invention can be used with patient specimens obtained by conventional methods from the eye, the nares at the back of the nose, cervix, vagina, urethra, rectum, throat, blood, serum, plasma, urine and the like. The reagents and pretreatment method may be used in any immunoassay where the presence of endogenous antibodies interferes with analyte detection, but are particularly useful with analytes that are not stable at a low pH.

Many different immunoassays can achieve an enhanced performance using the pretreatment method of the invention, including radioimmunoassays, immunoassays which employ ELISA procedures and immunoassays employing a variety of labels, including fluorescent and chemiluminescent labels. One such immunoassay includes the steps of contacting the extracted neutralized sample solution with a monoclonal antibody to the analyte immobilized on a solid phase, such as microplate well, bead, particle, tube or the like, incubating, adding a labeled polyclonal antibody that binds to the solid phase in amount related to the amount of analyte in the sample, incubating and detecting the label.

The amount and concentration of alkylating agent useful in a particular immunoassay will vary depending upon the sample type, i.e. serum or urogenital swab, concentration of the other immunoassay reagents, type of analyte and temperature at which pretreatment is conducted.

In certain immunoassays to detect the presence of microorganisms the analyte being detected is an acid sensitive lipopolysaccharide (LPS), such as the chlamydial antigen. Typically, in assays for such chlamydial antigens and similar antigens, the patient sample is pretreated with a detergent solution which includes alkali or alkaline earth metal ion. During the extraction step, endogenous anti-analyte antibodies are partially denatured or perturbed. With time, however, once the sample solution is neutralized the endogenous antibodies renature and will block recognition of the analyte by interfering with the binding of antibody reagent to the analyte during the immunoassay.

Although we do not wish to be bound by the following, we believe that the alkylating agents react with groups on antibodies that have been partially denatured or perturbed to prevent renaturation of the antibodies during the immunoassay.

One type of alkylating agent, particularly useful in an immunoassay for LPS is one that is active only at an alkaline pH, e.g. greater than 8.0, and inactive at a neutral or acid pH. Alkylating agents of this type include without limitation glutaraldehyde, formaldehyde, o-methylisourea, butanedione and cyclohexanedione. Such agents are particularly preferred because typically immunoassays are conducted at a neutral pH so they would not interfere with the performance of the assay.

Another type of alkylating agent of this invention is active at a neutral pH (pH 7.0–pH 8.0), and can be inactivated by the addition of a second reagent having amine groups such as a tertiary amine like Tris or a primary amine like glycine. Alkylating agents of this type include without limitation S-acetyl thioglycolic acid N-hydroxy succinimide.

The method of the present invention will be more easily understood by reference to the following examples which are illustrative and non-limiting.

EXAMPLE 1.—Chlamydia Immunoassay

A Kallestad Pathfinder® Chlamydia Microplate kit was used in performing the pretreatment method and the immunoassay. The Kallestad Pathfinder® Chlamydia Microplate kit included:

A sample treatment solution A (STS A) which includes 0.1N NaOH, 5 mM EDTA, 50 mg/ml Alizarin Yellow (2-hydroxy-5-[(4nitrophenyl)azo]benzoic acid, a dye that is yellow at a neutral pH below 10.2 and red at pH 12 and 0.05% 3[( 3-cholamidopropyl)-diamethylammoni-o]-1-propane sulfonate (CHAPS).

A sample treatment solution B (STS B) which includes 1.0 N HCl, 2M Tris Base, 3% $H_2O_2$.

The extraction method performed prior to the immunoassay described below included the steps of adding 1.0 ml of STS A to 0.1 ml of sample and incubating for 10 minutes and vortexed for 30 seconds. Then in order to determine the effectiveness of alkylating agents of the invention, 0.1 ml of an alkylating agent or buffer was added, vortexed for 10 seconds and then incubated for 10 minutes. Prior to conducting the immunoassay, 0.1 ml STS B was added and the sample solution vortexed for 10 seconds.

After extraction, an immunoassay was performed using the Kallestad Pathfinder® Microplate kit as described below.

A 100 µl aliquot of extracted sample was added to each Pathfinder® Microplate well to which a monoclonal antibody to chlamydia antibody is bound. The plate was incubated for 30 min, 26° C., STAT-FAX shaking incubator (Awareness Technologies). 50 µl polyclonal rabbit anti-chlamydia antibody reagent was added to each well and the plate was incubated for 30 min 26° C. STAT-FAX 2200.

Then 50 µl horseradish peroxidase conjugated to goat anti-rabbit was added to each well and the plate incubated 30 min 26° C. STAT-FAX 2200.

The wells of the plates were then washed 5 times on the LP-35 Microplate Washer (Diagnostics Pasteur, France) and 100 µl o-phenylenediamine in buffer was added to each well and the plate incubated for 30 minutes in the dark. 100 µl of a stop solution comprising $4NH_2SO_4$ was added and the microplates read on a LP-400 microplate reader (Diagnostic Pasteur, France) at OD 492/620.

EXAMPLE 2—Acid Sensitive Analyte

As mentioned above, the pretreatment method is particularly preferred for acid sensitive analytes such as lipopolysaccharide. We demonstrated that the antigenicity of LPS was effected when sample was treated with an acid but not with a base.

Acid Treatment: 1 ml chlamydia antigen in STS A:STS B (10:1) was treated with 30 µl 4M $H_3PO_4$ (pH 2.3) and the reaction was allowed to proceed 90 minutes and then was neutralized with 70 µl 2N NaOH (pH 8.1).

Base Treatment: 1 ml chlamydia antigen in STS A:STS B (10:1) was treated with 70 µl 2N NaOH (pH 12.5) and the reaction allowed to proceed 90 minutes before neutralization with 30 µl 4M $H_3PO_4$ (pH 2.3).

The results of acid and base treatment are shown in Table 1.

TABLE 1

| Preincubation Condition: | Clinical Pool 1 OD 492/620 | Clinical Pool 2 OD 492/620 | EB's 3.4 × 10⁻5 OD 492/620 | EB's 1.72 × 10⁻5 OD 492/620 |
| --- | --- | --- | --- | --- |
| No Treatment | 0.135 | 2.775 | 0.361 | 0.254 |
| Acid treated | 0.087 | 0.401 | 0.247 | 0.168 |
| Base Treated | 0.303 | 1.873 | 0.431 | 0.213 |

EXAMPLE 3—Alkylating Agents

The effectiveness of the various alkylating agents in modifying endogenous antibodies and enhance the EIA signal was demonstrated with seropositive plasma (human anti-chlamydia in plasma) and equine anti-chlamydia models. Human anti-chlamydia seropositive plasma or immunoaffinity purified equine anti-chlamydia were mixed with *Chlamydia trachomatis* Elementary Bodies (serovar L2, usually $1.5 \times 10^6$ EB's/ml final) and extracted as described in Example 1.

The effectiveness of each alkylating agent was assessed by comparison to sample treated with only buffer. As shown in Table 2, after the alkylating agents have been inactivated by addition of a neutralizing agent in STS B, an immediate enhancement of analyte detection is seen at time zero with the alkylating agents glutaraldehyde and cyclohexanedione as compared to treatment with just buffer.

TABLE 2

| | Treatments | | |
|---|---|---|---|
| | Time 0 hr post Extr. OD 492/620 | Time 120 hr post extr. OD 492/620 | % Change |
| Buffer | 1.479 ± 0.086 | 0.938 ± 0.048 | 37% drop |
| 1% Glutaraldehyde | 1.821 ± 0.035 | 1.743 ± 0.073 | 4% drop |
| 1% Glutaraldehyde/25 mM DTT | 1.895 ± 0.078 | 1.975 ± 0.129 | 4% increase |
| 50 mM Cyclohexanedione | 1.851 ± 0.031 | 1.546 ± 0.009 | 17% drop |
| 50 mM Cyclohexanedione/25 mM DTT | 2.379 ± 0.137 | 2.488 ± 0.026 | 4% increase |
| 25 mM DTT | 1.977 ± 0.051 | 2.241 ± 0.059 | 13% increase |

The results shown in Table 2 demonstrate that the alkaline extraction alone without an alkylating agent will perturb anti-chlamydia antibody rendering it less able to interfere with analyte detection. Over time, however, the alkaline perturbed antibodies renatured in the sample with buffer alone and effectively neutralized EIA signal by interfering with antigen capture or detection in the Pathfinder format.

At 0 hr post extraction, (Table 2) the buffer treated sample has an OD 20% and 22% below those of samples extracted in the presence of 1% glutaraldehyde with and without DTT, respectively. At 120 hours post extraction, the samples extracted in the presence of just buffer dropped 37% as compared to the extractions with 1% glutaraldehyde and 50 mM cyclohexanedione which dropped slightly. Combining 25 mM DTT with the glutaraldehyde and cyclohexanedione resulted in a slight increase in signal from time zero.

EXAMPLE 4—Glutaraldehyde

Chlamydia Elementary Body preparations were mixed with various concentrations of equine anti-chlamydia, pretreated after extraction with detergent with the 1% glutaraldehyde/25 mM DTT or buffer and carried through the EIA procedure described above. Samples pretreated with the alkylating/cross linking glutaraldehyde show a marked increase in signal, shown in FIG. 1, proportional to buffer treated samples at time zero (post extraction) at all concentrations of equine anti chlamydia except 0.2 ug/ml, which approached the limits of neutralization activity. Human anti-chlamydia (P1) demonstrated a nearly equivalent neutralization effect as 1.6 ug/ml equine anti-chlamydia in the absence of glutaraldehyde.

The influence of equine or human anti-chlamydia on EIA signal generation were evaluated at several timepoints post-extraction. In the absence of glutaraldehyde, the sensitivity of the assay at zero hours post extraction was much greater than at 24 or 48 hours post-extraction as seen by a decrease in OD shown in FIG. 2. In the presence of glutaraldehyde/DTT, as shown in FIG. 3 the differences were not as pronounced over time and the overall detection of chlamydial antigen was not blocked by equine-anti-chlamydia.

The presence of human anti-chlamydia (Hu×C) in urogenital clinical specimens, and the effect of pretreatment of the sample with glutaraldehyde/DTT, was further demonstrated by western blot immunoassay procedures. Clinical specimens were pretreated as described above in the presence or absence of glutaraldehyde/DTT and monitored for a loss of EIA signal, indicative of the presence of Hu×C. It was noted that those samples with the greatest loss of EIA signal had immunoreactive Hu×Chlamydia (MOMP, Major Outer Membrane Protein) as shown in FIG. 4. In the matched samples containing glutaraldehyde, no immunoreactive human anti-MOMP (Hu× MOMP) was detected.

EXAMPLE 5—Pretreatment with Alkylating Agents at an Alkaline PH

Table 3 shows the results on analyte detection when different concentrations of various alkylating agents were used. 0.1 ml of chlamydia antigen was added to seropositive plasma and mixed with STS A, vortexed for 10 seconds and then incubated for 10 minutes. 0.1 ml alkylating agent or buffer was then added, the solution vortexed for 10 seconds and incubated for 10 minutes. Prior to conducting the immunoassay, 0.1 ml STS B was added and the sample solution vortexed for 10 seconds. As can be seen from Table 3, the lower concentrations of alkylating agents were not as effective 48 hours post extraction in eliminating interference of endogenous antibodies but were more effective than just buffer at 0 hr and 24 hr post extraction.

TABLE 3

| | Treatments | | |
|---|---|---|---|
| | 0 hr Post Extraction Sero Pos Plasma | 24 hr Post Extraction Sero Pos Plasma | 48 hr Post Extraction Sero Pos Plasma |
| 1% GLUTERALDEHYDE | 1.385 ± 0.062 | 1.598 ± 0.049 | 1.311 ± 0.076 |
| 0.5% GLUTERALDEHYDE | 1.520 ± 0.080 | 1.615 ± 0.072 | 0.425 ± 0.063 |
| 1% FORMALDEHYDE | 1.549 ± 0.230 | 1.512 ± 0.025 | 1.321 ± 0.084 |
| 0.5% FORMALDEHYDE | 1.506 ± 0.115 | 1.254 ± 0.116 | 0.989 ± 0.217 |
| 25 mM BUTANEDIONE | 1.439 ± 0.006 | 1.277 ± 0.086 | 0.944 ± 0.123 |
| 12.5 mM BUTANEDIONE | 1.351 ± 0.120 | 1.145 ± 0.113 | 0.726 ± 0.173 |
| BUFFER | 1.238 ± 0.120 | 0.825 ± 0.044 | 0.694 ± 0.036 |

In addition to pretreatment at an alkaline pH with glutaraldehyde, 50 mM O-methylisourea (OMIU) and 50 mM cyclohexanedione (CHD) were added to sample solution following extraction in STS A and an immunoassay performed as described in Example 1. Both agents resulted in improved immunoassay results over time and immunoassay performance was enhanced further when the alkylating agents were combined with DTT.

The results of these experiments over a 5 day post extraction period are shown below in Table 4.

While a preferred embodiment of the present invention has been described, it should be understood that various changes, adaptations and modifications may be made therein without departing from the spirit of the invention and the scope of the appended claims.

What is claimed is:

1. An improved immunoassay for assaying an analyte within a patient sample containing antibodies that interfere with analyte detection, the analyte being antigenic comprising the following steps:

TABLE 4

| | Time 5 days | | |
|---|---|---|---|
| | 0 Days Post Extraction | 3 Days Post Extraction Treatments | 5 Days Post Extraction |
| | Sero Positive Plasma OD 492/620 | Sero Positive Plasma OD 492/620 | Sero Positive Plasma OD 492/620 |
| Buffer | 1.479 ± 0.230 | 0.685 ± 0.040 | 0.938 ± 0.048 |
| 1% GA | 1.821 ± 0.035 | 1.109 ± 0.051 | 1.743 ± 0.073 |
| GA/DTT | 1.895 ± 0.078 | 1.337 ± 0.036 | 1.975 ± 0.129 |
| 50 mM OMIU | 1.540 ± 0.169 | 0.694 ± 0.048 | 0.957 ± 0.043 |
| OMIU/DTT | 2.192 ± 0.057 | 1.773 ± 0.167 | 2.228 ± 0.194 |
| 250 mM CHD | 1.851 ± 0.031 | 1.205 ± 0.016 | 1.546 ± 0.009 |
| CHD/DTT | 2.379 ± 0.137 | 1.908 ± 0.056 | 2.488 ± 0.026 |
| 50 mM DTT | 1.977 ± 0.051 | 1.702 ± 0.036 | 2.241 ± 0.059 |

EXAMPLE 6—Pretreatment with Alkylating Agents at a Neutral PH

Although alkylating agents that are active at an alkaline pH are preferred in immunoassays for LPS, alkylating agents active at a neutral pH can also be used. We mixed 2 ml EBs (1:16, $3.12\times10^6$) and 40 µl equine anti-chlamydia (100 µg/ml, final 2 µg/ml) and used 0.1 ml aliquots of the EB-antibody mixture as a sample. Aliquots were added to 8 tubes and extracted with 1 ml STS A, vortexed and incubated for 10 minutes at room temperature. 100 µl HCl/phosphate buffer was added, the pH of which was preadjusted so that when combined with the sample-STS A solution the pH would be 8.0. 50 mM S-acetyl thioglycolic acid N-hydroxy succinimide (SATA) was added and the solution incubated for 60 minutes at room temperature. 0.1 ml 1M Tris (pH 8) which is a tertiary amine was then added to inactivate the alkylating agent.

The samples were assayed using the chlamydia immunoassay method described in Example 1. Buffer alone resulted in only 0.365±0.21 OD at 472/620. Treatment of sample with SATA at neutral pH, resulted in improved immunoassay results of 2.26± 0.75, which was close to the EB sample OD in the absence of equine anti-chlamydia.

a) contacting the sample with an alkylating agent capable of alkylating groups on the anti-analyte antibodies at a pH not less than 7.0 to modify the antibodies to render them incapable of interfering with analyte detection, the alkylating agent being one which does not effect the antigenicity of the analyte;

b) inactivating the alkylating agent, and then c) performing an immunoassay on the sample to assay the analyte in the presence of the modified antibody.

2. The improved immunoassay of claim 1 wherein the analyte is acid sensitive.

3. The improved immunoassay of claim 2 wherein the analyte is a lipopolysaccharide antigen.

4. The improved immunoassay of claim 3 wherein the lipopolysaccharide antigen is from a microorganism selected from the group consisting of *Chlamydia trachomatis, Chlamydia psittaci, Salmonella typhimurium, Neisseria gonorrhoeae* and *Escherichia coli.*

5. The improved immunoassay of claim 1 wherein the alkylating agent is glutaraldehyde, formaldehyde, o-methylisourea, cyclohexanedione, butanedione or S-acetyl thioglycolic acid N-hydroxy succinimide.

6. The improved immunoassay of claim 1 wherein the alkylating agent is also capable of cross linking groups on the antibodies.

7. The improved immunoassay of claim 1 wherein the alkylating agent is activated at an alkaline pH and is inactivated by neutral pH and wherein the inactivating step comprises neutralizing the pH of the sample.

8. The improved immunoassay of claim 3 further comprising the steps of contacting the sample with an appropriate extraction detergent at an alkaline pH to release the lipopolysaccharide antigen prior to or simultaneously contacting sample with the alkylating agent.

9. An immunoassay kit for assaying an analyte in a patient sample containing endogenous antibodies that interfere with the detection of analyte, the immunoassay kit comprising immunoassay reagents for performing an immunoassay on the sample for assaying the analyte, an alkylating agent capable of alkylating groups on the antibodies at a pH not less than 7.0 to modify the endogenous antibodies to prevent them from binding to the analyte, and an inactivating agent for inactivating the alkylating agent, the immunoassay reagents being operable in the presence of the inactivating agent and inactivated alkylating agent.

10. The immunoassay kit of claim 9 wherein the alkylating agent is glutaraldehyde, formaldehyde, o-methylisourea, glyceraldehyde or S-acetyl thioglycolic acid N-hydroxy succinimide.

11. The immunoassay kit of claim 9 wherein the alkylating agent is activated at an alkaline pH and inactivated at a neutral pH and the inactivating agent is a neutralizing agent.

12. The immunoassay kit of claim 11 further including a detergent and alkali earth metal reagent for extracting the analyte from the sample and wherein the analyte is a lipopolysaccharide antigen.

13. An improved immunoassay for assaying for an acid sensitive analyte within a patient sample containing antibodies that interfere with analyte detection, the analyte being antigenic comprising the following steps:

a) after the sample has been treated with an alkaline extraction to release analyte contacting the sample with an alkylating agent capable of alkylating groups on the anti-analyte antibodies at a pH not less than 7.0 to modify the antibodies to render them incapable of interfering with analyte detection, the alkylating agent being one which does not effect the antigenicity of the analyte;

b) inactivating the alkylating agent, and then c) performing an immunoassay on the sample to assay the analyte in the presence of the modified antibody.

14. An improved immunoassay for assaying for a lipopolysaccharide antigen within a patient sample containing antibodies that interfere with analyte detection, the analyte being antigenic comprising the following steps:

a) after alkaline detergent extraction of the sample to release the lipopolysaccharide antigen contacting the sample with an alkylating agent capable of alkylating groups on the anti-analyte antibodies at a pH not less than 7.0 to modify the antibodies to render them incapable of interfering with analyte detection, the alkylating agent being one which does not effect the antigenicity of the lipopolysaccharide antigen;

b) inactivating the alkylating agent, and then c) performing an immunoassay on the sample to assay the lipopolysaccharide antigen in the presence of the modified antibody.

* * * * *